United States Patent
Tanaka et al.

(10) Patent No.: US 8,395,128 B2
(45) Date of Patent: Mar. 12, 2013

(54) RADIATION TOMOGRAPHY APPARATUS

(75) Inventors: Kazumi Tanaka, Otsu (JP); Yoshihiro Inoue, Kyoto (JP); Masaharu Amano, Ibaraki (JP); Tetsuro Mizuta, Kyoto (JP); Atsushi Ohtani, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 24 days.

(21) Appl. No.: 13/201,549

(22) PCT Filed: Feb. 16, 2009

(86) PCT No.: PCT/JP2009/000606
§ 371 (c)(1),
(2), (4) Date: Aug. 15, 2011

(87) PCT Pub. No.: WO2010/092623
PCT Pub. Date: Aug. 19, 2010

(65) Prior Publication Data
US 2011/0297840 A1    Dec. 8, 2011

(51) Int. Cl.
*G01J 1/42* (2006.01)
(52) U.S. Cl. .................................................. 250/393
(58) Field of Classification Search .................. 250/393, 250/362, 363.01–363.1; 378/98.8
See application file for complete search history.

(56) References Cited

U.S. PATENT DOCUMENTS

| | | | |
|---|---|---|---|
| 7,564,945 B2* | 7/2009 | Kim | 378/65 |
| 2004/0057557 A1* | 3/2004 | Nafstadius | 378/209 |
| 2009/0005671 A1* | 1/2009 | Kreischer et al. | 600/411 |

FOREIGN PATENT DOCUMENTS

| | | |
|---|---|---|
| JP | 4-268484 A | 9/1992 |
| JP | 2005-312930 A | 11/2005 |
| JP | 2008-307083 A | 12/2008 |

OTHER PUBLICATIONS

Yamaya et al., "Preliminary performance evaluation of the prototype system for a brain DOI-PET scanner:jPET-D4," 2004, IEEE Nuclear Science Symposium Conference Record, vol. 4, pp. 2610-2614.*
International Search Report for the Application No. PCT/JP2009/000606 mailed Apr. 28.2009.

* cited by examiner

*Primary Examiner* — Kiho Kim
(74) *Attorney, Agent, or Firm* — Cheng Law Group, PLLC (57) ABSTRACT

One purpose of this invention is to provide radiation tomography apparatus with easier maintenance. A specific approach for this purpose is as follows. That is, a detector ring in the radiation tomography apparatus includes two or more rings. Moreover, a ring moves as to approach a next ring, whereby both the rings are connected. If radiation tomography is conducted while a clearance is provided between the rings, detection sensitivity of the detector ring decreases due to the clearance. On the other hand, according to this invention, the ring moves as to approach the next ring, which results in a narrower clearance. Accordingly, radiation that is not observed may be reduced as much as possible.

20 Claims, 8 Drawing Sheets

RADIATION TOMOGRAPHY APPARATUS

TECHNICAL FIELD

This invention relates to radiation tomography apparatus that images radiation emitted from a subject. Particularly, this invention relates to radiographic apparatus having a field that is wide enough to image a body portion of the subject at one time.

BACKGROUND ART

In medical fields, radiation emission computed tomography (ECT: Emission Computed Tomography) apparatus is used that detects an annihilation radiation (for example, gamma rays) pair emitted from radiopharmaceutical that is administered to a subject and is localized to a site of interest for acquiring sectional images of the site of interest in the subject showing radiopharmaceutical distributions. Typical ECT equipment includes, for example, a PET (Positron Emission Tomography) device and an SPECT (Single Photon Emission Computed Tomography) device.

A PET device will be described by way of example. The PET device has a detector ring with block radiation detectors arranged in a ring shape. The detector ring is provided for surrounding a subject, and allows detection of radiation that is transmitted through the subject.

Figure 10:
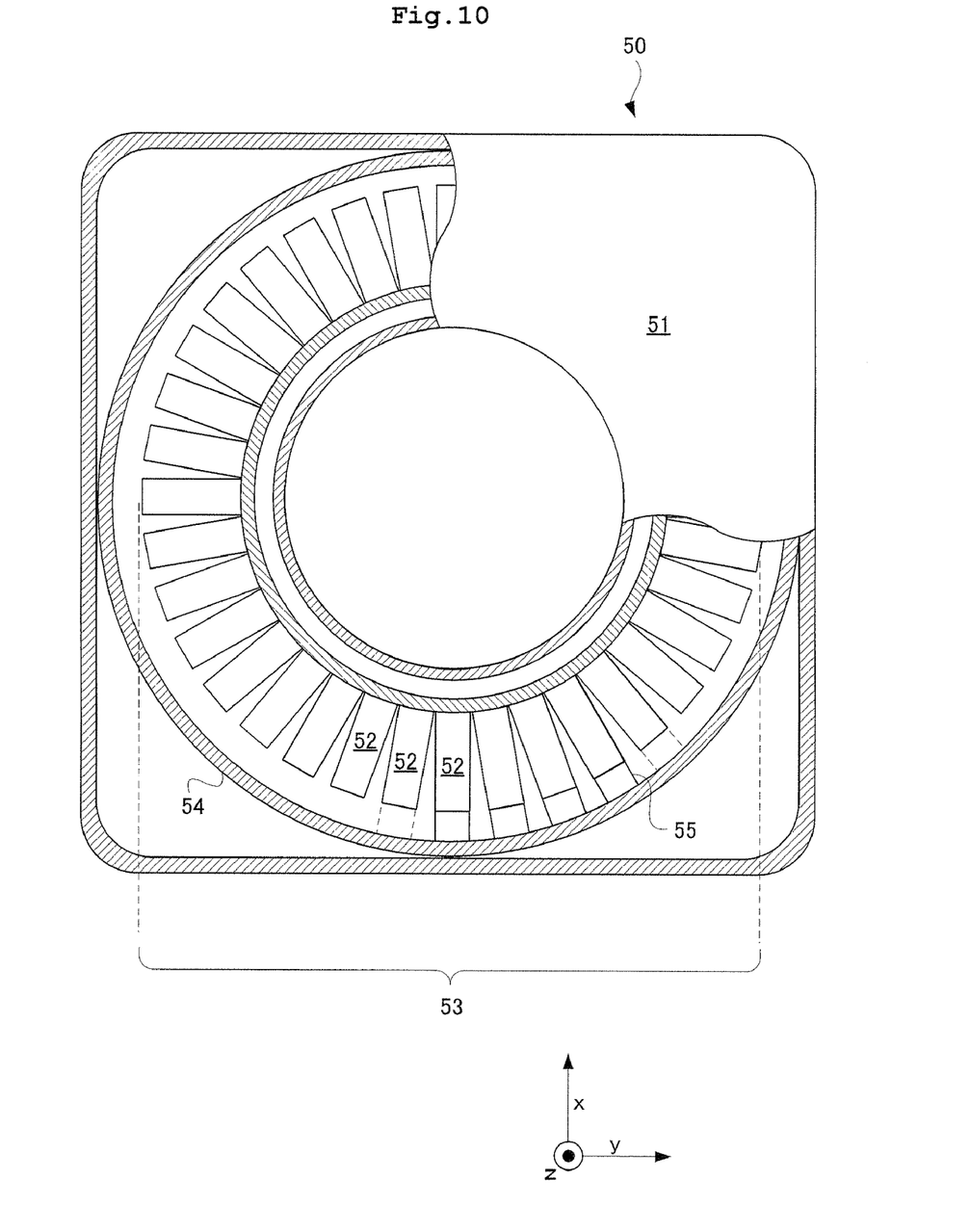
FIG. 10 is a sectional cut-away view showing the conventional configuration.

First, description will be given of a configuration of a conventional PET device. As shown in FIG. 10, a conventional PET device 50 includes a gantry 51 with an introducing hole that introduces a subject, a detector ring 53 having block radiation detectors 52 for detecting radiation being arranged inside the gantry 51 as to surround the introducing hole, and a support member 54 provided as to surround the detector ring 53. Each of the radiation detectors 52 has a bleeder unit 55 with a bleeder circuit. The bleeder unit 55 is provided between the support member 54 and the radiation detector 52 for connecting the support member 54 and the radiation detector 52. Such PET device is described, for example, in Patent Literature 1.

The PET device determines annihilation radiation pairs emitted from radiopharmaceutical. Specifically, an annihilation radiation pair emitted from inside of a subject M is a radiation pair having traveling directions opposite by 180 degrees.

[Patent Literature 1]
Japanese Patent Publication No. 2005-312930

DISCLOSURE OF THE INVENTION

[Summary of the Invention]
However, the conventional radiation tomography apparatus has the following drawbacks. Specifically, a field of view is smaller in the conventional radiation tomography apparatus. Where the field of view expands in a direction of a body axis of subject (z-direction in FIG. 10) in accordance with the conventional configuration, a detector ring 53 extends in the direction of the body axis of subject. With such configuration, however, where one of radiation detectors 52 forming the detector ring 53 is out of order, the huge detector ring 53 extending in the z-direction should be disassembled for replacement of the radiation detector 52. Such configuration having difficulty in maintenance cannot be employed.

This invention has been made having regard to the state of the art noted above, and its object is to provide radiation tomography apparatus with high detection sensitivity and easy maintenance.

[Means for Solving the Problem]
This invention is constituted as stated below to achieve the above object. That is, one embodiment according to Claim I includes a first ring having radiation detectors for detecting radiation from a subject annularly arranged, a second ring having the radiation detectors annularly arranged, a gantry for containing both the rings, a first moving device for moving the first ring relative to the gantry, and a movement control device for controlling the first moving device. Both the rings are spaced away by a given clearance as to share each central axis. The first ring moves as to approach the second ring in connection with control by the movement control device, whereby both the rings are connected. The gantry comprises a first housing for containing the first ring, and a second housing for containing the second ring. Both the housings being mechanically removable.

[Operation and Effect]
The foregoing detector ring in the radiation tomography apparatus includes the first ring and the second ring. The first ring and the second ring are contained in the gantry. With such configuration, merely arranging housings may realize expansion of the field of view. According to this invention, two or more conventional detector rings are connected to manufacture radiation tomography apparatus having a large field of view.

Such configuration may provide radiation tomography apparatus with easier maintenance. For instance, when there arises a need to replace the first ring, the first housing is disconnected from the second housing. Consequently, the first ring contained in the first housing may be drawn out. With such specific configuration, the first housing is pulled out relative to the second housing in a direction perpendicular to a central axis, whereby the first ring is drawn out. The first ring is spaced away from the second ring, and a given clearance is provided between both the rings. Then, the first housing is pulled out under this state. Consequently, no interference of the first ring occurs with the second housing.

Moreover, both rings are connected through moving the first ring as to approach the second ring. Such configuration may provide radiation tomography apparatus with high sensitivity. If radiation tomography is conducted while a clearance is provided between both rings, some radiation emits from inside of the detector ring through the clearance. Such radiation does not enter into the radiation detector, and thus is not observed. Accordingly, the detector ring has poor detection sensitivity due to the clearance. On the other hand, according to this invention, the first ring moves as to approach the second ring, which results in a narrower clearance. Accordingly, radiation that is not observed may be reduced as much as possible.

Moreover, the gantry is held stationary when the foregoing first ring moves.

[Operation and Effect]
The above configuration represents a specific embodiment of the radiation tomography apparatus according to this invention. Specifically, the first ring moves relative to the gantry, whereby both the rings are connected. The gantry does not move to connect both the rings. In other words, in the radiation tomography apparatus, the first ring moves toward the second ring in the gantry. Accordingly, the first moving device for moving the first ring may be reduced in size.

Moreover, provided are a third ring having radiation detectors mentioned above annularly arranged, and a second moving device for moving the second ring relative to the second housing. The first ring, the second ring, and the third ring are spaced away in this order by a given clearance as to share each central axis. The first ring and the second ring synchronously move as to approach the third ring through control by the movement control device, whereby the three rings are connected. Such configuration is more desirable.

[Operation and Effect]

Such configuration may provide radiation tomography apparatus with easier control. Specifically, the detector ring concerning the foregoing configuration includes three rings. The first ring and the second ring synchronously move as to approach the third ring, whereby the three rings are connected. In other words, the movement control device controls each ring en bloc, which leads to simpler control thereof.

The second housing is placed between the first housing and the third housing. The second ring is connected to the first ring and the third ring. Here, it is assumed that there arises a need to replace a radiation detector forming the second ring that is out of order. In this case, it is assumed that the connected three rings are spaced away, and the second ring is contained in the second housing. When the second housing is pulled out under this state, the second ring may be easily drawn out.

Moreover, the first ring has a width in the above central axis that is smaller than the first housing in the central axis. Such configuration is more desirable.

[Operation and Effect]

The width of the first ring in the central axis (the direction of the body axis of subject) that is smaller than that of the first housing in the same direction may avoid interference of the first ring with the second housing when the first housing is pulled out for maintenance.

Moreover, a coincidence device is provided for performing coincidence of the foregoing radiation pairs. The first moving device moves the first ring such that a housing state and a connection state are alternately repeated. Here, the housing state is a state where the first ring is housed in the first housing, and the connection state is a state where the first ring is connected to the second. The coincidence device counts a number of radiation pairs when the first ring is in either of both the states. Such configuration is more desirable.

[Operation and Effect]

With the foregoing configuration, various types of methods for detecting radiation may be achieved. That is, the radiation tomography apparatus may count the number of radiation pairs under any of the housing state and the connection state. In other words, radiation may be detected under any of both the states. Simply in the light of increasing a dose of radiation to be detected, it is preferable for the first ring to be under the connection state upon imaging. On the other hand, a clearer sectional image having reduced noises may sometimes be acquired when the first ring is under the housing state depending on distribution of occurrence sites of radiation in the subject. As above, the characteristic that the first ring moves may efficiently be employed also in taking a radiation tomography image.

In addition to both the states, the foregoing coincidence device counts the number of radiation pairs under an intermediate state between both the states. Such configuration is more desirable.

[Operation and Effect]

With the foregoing configuration, more various types of methods for detecting radiation may be achieved. A clearer sectional image having reduced noises may sometimes be acquired under the intermediate state. According to the foregoing configuration, the state of the first ring suitable for imaging may be searched for. Moreover, in the foregoing configuration, radiation may be detected while the housing state, the connection state, and the intermediate state are repeated.

Moreover, provided are a ring position acquiring device for acquiring a position of the first ring, and a positional information correction device for correcting positional information on a radiation pair outputted from the first ring in accordance with positional information from the ring position acquiring device. Such configuration is more desirable.

[Operation and Effect]

The above construction represents a specific embodiment of this invention. Specifically, the foregoing configuration is provided with the ring position acquiring device and the positional information correction device. The first ring moves relative to the subject. Accordingly, a position indicated by information on the radiation pair that is outputted from the first ring is shifted relative to the subject. In the foregoing configuration, the positional information outputted from the first ring is corrected in accordance with the position of the first ring, whereby a position of the radiation pair relative to the subject may be acquired. In so doing, a radiation tomography image having no distortion may be acquired without influences of movement of the first ring when radiation is detected while the first ring moves relative to the subject.

Moreover, in addition to the foregoing configuration, further provided is a top board that extends in the central axis direction and is inserted into an inside portion of the first ring. Additionally, provided is an image generation device having (A) a radiation source that allows rotation relative to the top board around the central axis, (B) a radiation detecting device that allows rotation relative to the top board around the central axis, (C) a support device for supporting the radiation source and the radiation detecting device, (D) a rotating device for rotating the support device, and (E) a rotation control device for controlling the rotating device. Such configuration is more desirable.

[Operation and Effect]

According to the above configuration, radiation tomography apparatus may be provided that allows acquisition of both images of an internal subject structure and pharmaceutical distribution. In general, a PET device may obtain information on pharmaceutical distribution. However, it may sometimes be necessary to conduct diagnosis referring to the sectional image having internal organs and tissue of the subject falling therein. According to the above configuration, both images of the internal structure of the subject and pharmaceutical distribution may be acquired.

Consequently, superimposing both images may realize generation of a composite image suitable for diagnosis.

[Effect of the Invention]

The foregoing detector ring in the radiation tomography apparatus includes the first ring and the second ring. Moreover, the first ring moves as to approach the second ring, whereby both the rings are connected. Such configuration may provide radiation tomography apparatus with high sensitivity. If radiation tomography is conducted while a clearance is provided between both the rings, some radiation emits from inside of the detector ring through the clearance. Such radiation does not enter into the radiation detector, and thus is not observed. Accordingly, the detector ring has poor detection sensitivity due to the clearance. On the other hand, according to this invention, the first ring moves as to approach the second ring, which results in a narrower clearance. Accordingly, radiation that is not observed may be reduced as much as possible.

DESCRIPTION OF REFERENCES d given clearance
1 radiation detector
9 radiation tomography apparatus
11a first housing
11b second housing
12c center unit (third ring)
12d quasi-center ring (second ring)
12e periphery ring (first ring)
17 ring position acquiring section (ring position acquiring device)
21 coincidence section (coincidence device)
22 positional information correction section (positional information correction device)
39 ring moving mechanism (first moving device, second moving device)
40 ring movement controller (movement control device)
41 rotating mechanism (rotating device)
42 rotation controller (rotation control device)
43 X-ray tube (radiation source)
44 FPD (radiation detecting device)
47 support portion (support device)

EMBODIMENT 1

<Whole Configuration of Radiation Tomography Apparatus>

Figure 1:
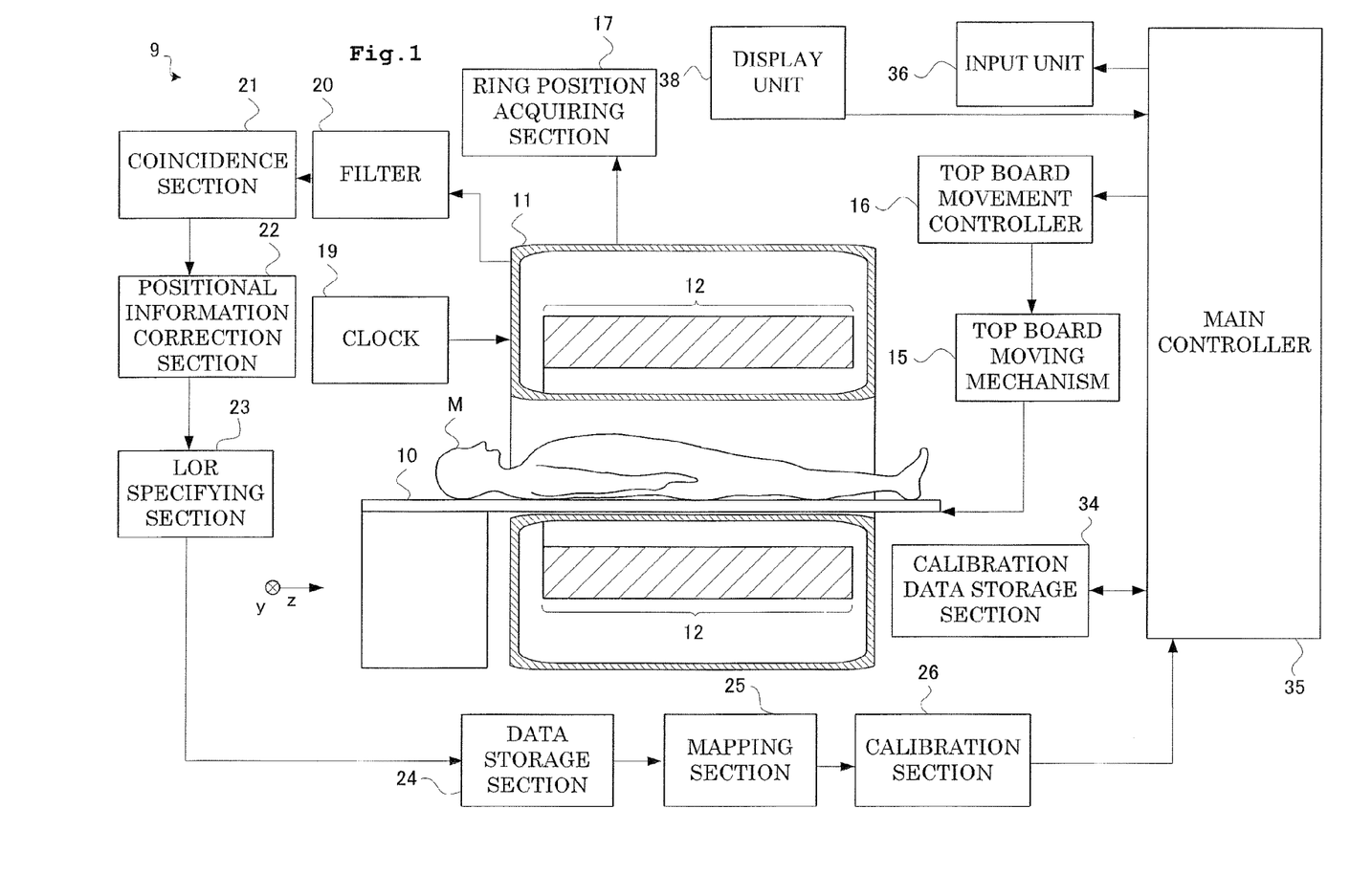
FIG. 1 is a functional block diagram showing a configuration of radiation tomography apparatus according to Embodiment 1.

Each embodiment of radiation tomography apparatus according to this invention will be described hereinafter with reference to the drawings. FIG. 1 is a functional block diagram showing a configuration of radiation tomography apparatus according to Embodiment 1. As shown in FIG. 1, the radiation tomography apparatus 9 according to Embodiment 1 includes a top board 10 for placing a subject M on the back thereof, and a gantry 11 with a through hole for surrounding the subject M. The top board 10 is provided as to pass through an opening of the gantry 11. The top board 10 freely moves in and out along a direction where the opening of the gantry 11 extends. A top board moving mechanism 15 slides the top board 10 as above. A top board movement controller 16 controls the top board moving mechanism 15.

The gantry 11 includes a detector ring 12 inside thereof that detects annihilation gamma-ray pairs from the subject M. The detector ring 12 is tubular and extends in a body axis direction z of the subject M (corresponding to the extension direction of this invention.) The detector ring 12 has a length around 1.8 m. That is, the detector ring 12 extends as to completely cover at least a body portion of the subject M. A clock 19 sends out time information to the detector ring 12. Time information about when gamma rays were acquired is given to detection data outputted from the detector ring 12, and inputted into a filter 20 mentioned later.

Figure 3:
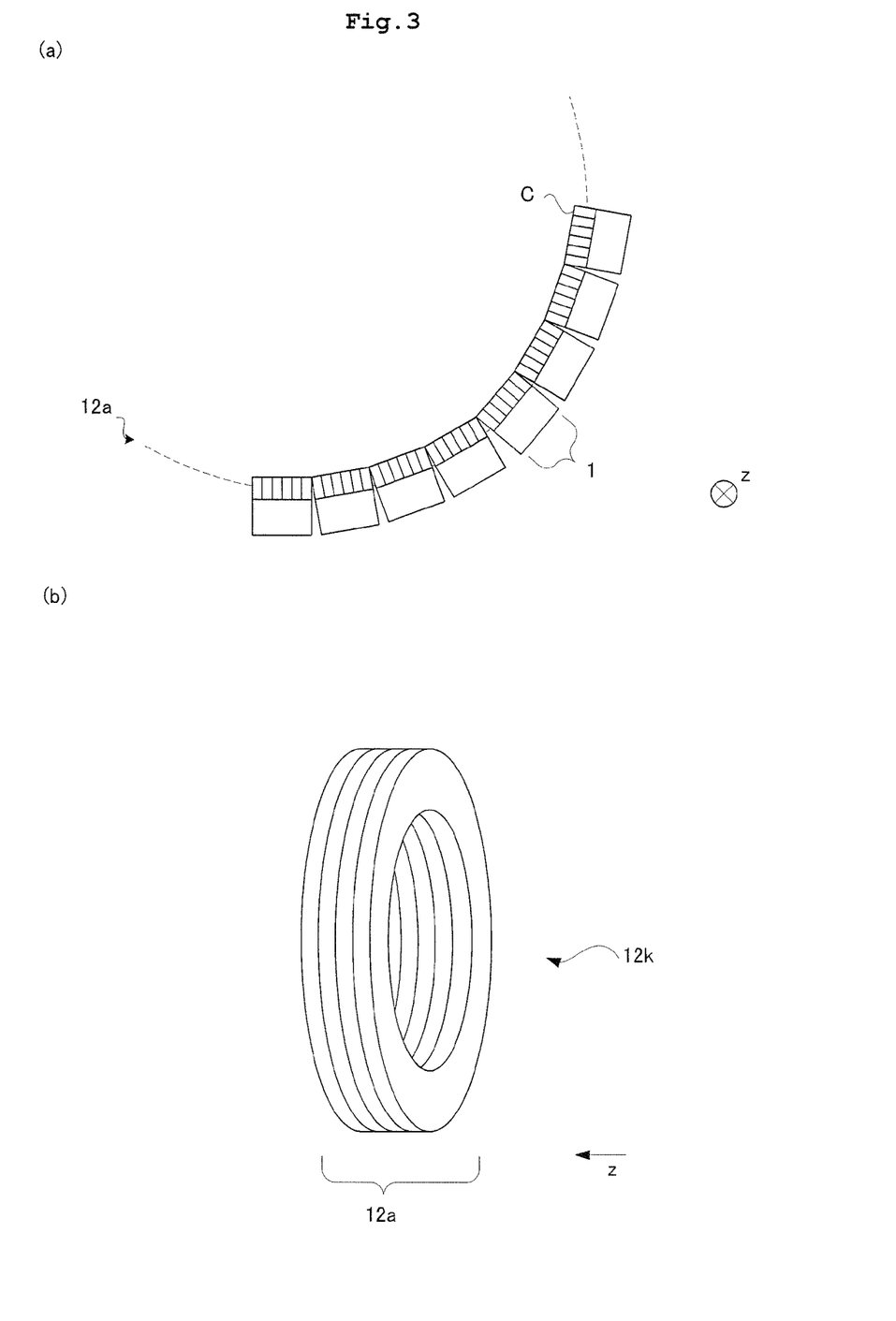
FIG. 3 conceptually shows a configuration of a ring according to Embodiment 1.

The ring unit has two or more rings 12a mentioned above connected to one another in the direction of the body axis. Specifically, the detector ring 12 is formed through connecting the rings 12a as to share central axes thereof (see FIG. 6.) The ring 12a has block radiation detectors 1 arranged in a ring shape. Assumed that a width per one radiation detector 1 is approximately 5 cm, four radiation detectors 1 are, for example, to be arranged in the ring 12a in the z-direction (the central axes of the rings 12a). See FIG. 3(b). Then, seven rings 12a having a thickness of approximately 20 cm are arranged in the z-direction to form the detector ring 12 that covers the subject (see FIG. 6.) The "ring" in the specification herein expresses seven annular members that form the detector ring 12.

Figure 2:
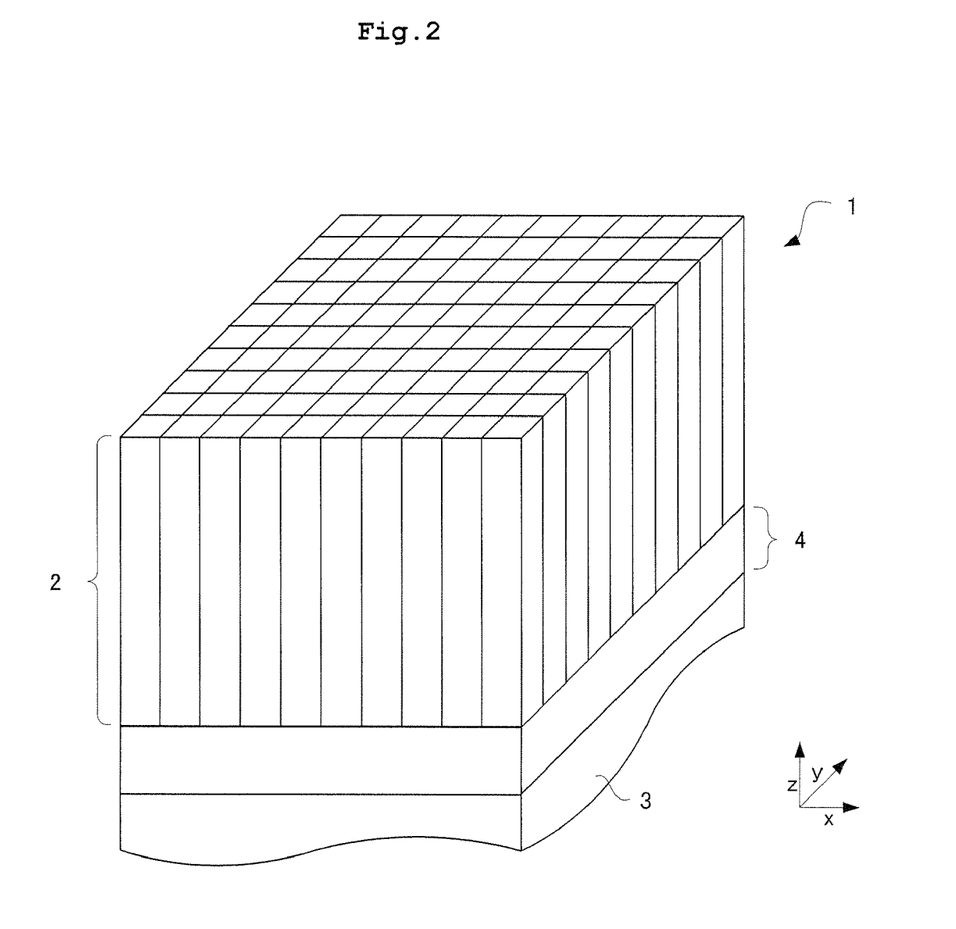
FIG. 2 is a perspective view showing a configuration of a radiation detector according to Embodiment 1.

Next, simple description will be given of a configuration of the radiation detector 1. FIG. 2 is a perspective view showing a configuration of the radiation detector according to Embodiment 1. As shown in FIG. 2, the radiation detector 1 includes a scintillator 2 that converts radiation into fluorescence, and a light detector 3 that detects fluorescence. A light guide 4 is provided between the scintillator 2 and the light detector 3 for receiving fluorescence.

The scintillator 2 has two or more scintillation counter crystals arranged in a two-dimensional array. Each of the scintillation counter crystals C is composed of Ce-doped $Lu_{2(1-X)}Y_{2N}SiO_5$ (hereinafter referred to as LYSO.) The light detector 3 allows determination about which scintillation counter crystal emits fluorescence as well as intensity of fluorescence and time when fluorescence is generated. Here, the scintillator 2 having the configuration of Embodiment 1 is only exemplification of an aspect that may be adopted. Consequently, the configuration of this invention is not limited to this.

Description will be given of a configuration of the ring 12a. According to Embodiment 1 shown in FIG. 3, the ring 12a is formed through arranging around 100 radiation detectors 1 in a circular ring shape. Consequently, the through hole 12k is of 100-sided polygon, for instance, seen thereof from the z-direction. The through hole 12k extends in the z-direction, and has a shape of a 100-sided prism.

Figure 4:
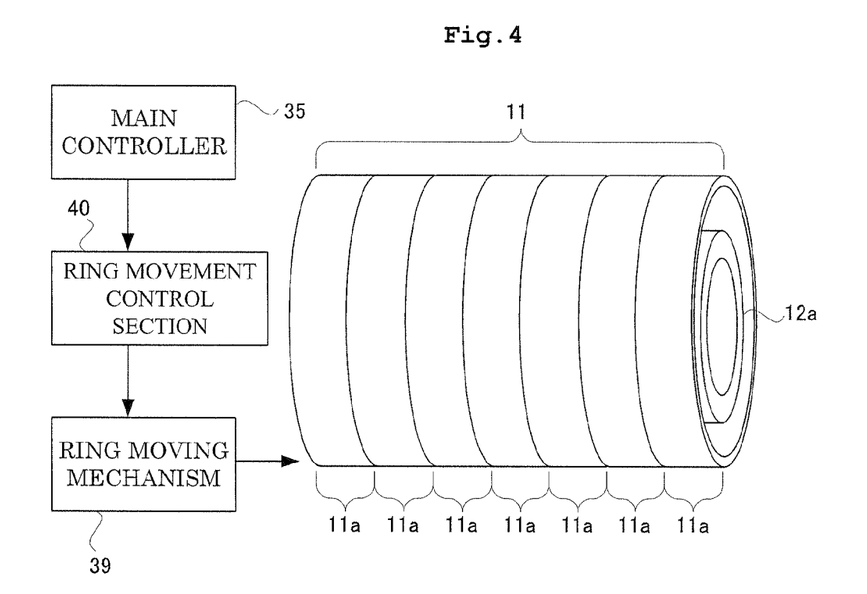
FIG. 4 is a perspective view showing a configuration of a gantry according to Embodiment 1.

Description will be given of the gantry 11. As shown in FIG. 4, the radiation tomography apparatus according to Embodiment 1 has the gantry 11 formed by connecting two or more housings 11a in the z-direction. The housing 11a has an annular shape having a width of approximately 25 cm in the z-direction. The number thereof is seven, which is equal to that of the foregoing ring 12a. Each ring 12a is contained in the housing 11a, and does not protrude from the housing 11a in the z-direction.

The ring moving mechanism 39 is provided between the ring 12a and the housing 11a for moving in and out the ring 12 relative to the housing 11a in the z-direction. In FIG. 4, the ring moving mechanism 39 is provided in a single housing 11a. Actually, the ring moving mechanism 39 is provided in each of the seven housings 11a. Here, the ring moving mechanism 39 follows control of the ring movement control section 40. The main controller 35 has control over the ring movement control section 40. The ring moving mechanism corresponds to the first and second moving devices in this invention. The ring movement mechanism corresponds to the movement control device in this invention.

Figure 5:
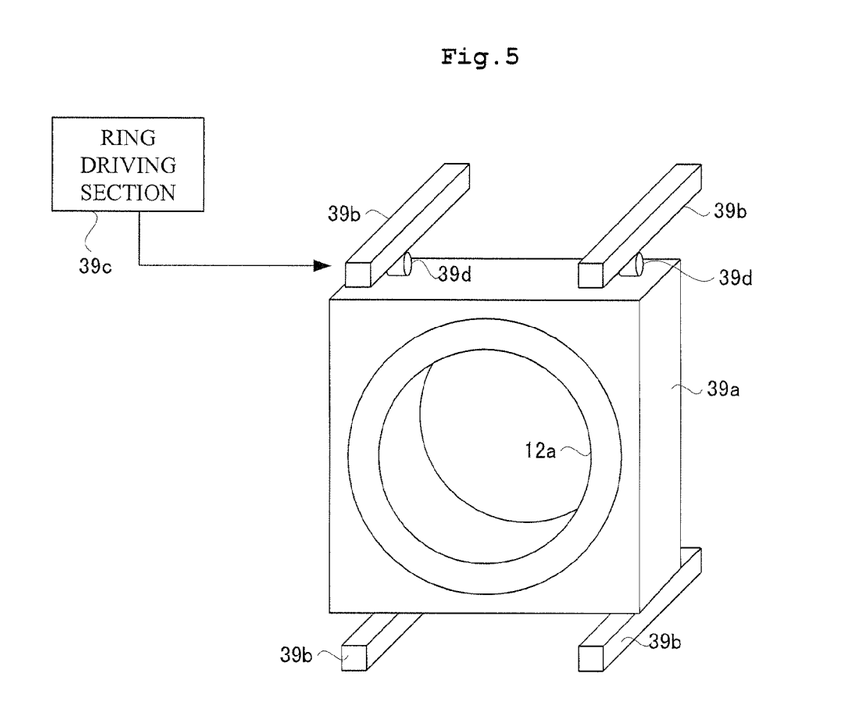
FIG. 5 is a perspective view showing a configuration of a ring moving mechanism according to Embodiment 1.

FIG. 5 shows the ring moving mechanism 39 having a support portion 39a for supporting the ring 12a, four rails 39b for supporting four sides of the rectangular supporting portion 39a, a ring driving section 39c such as a motor, and a rotation member 39d driven by the ring driving section 39c and provided on the support section 39c. Each of the rails 39b is fixed on the housing 11a. The rotation member 39d is provided on each rail 39d, and moves on the surface of the rail 39b while rotating. The ring driving section 39c drives the rotation member 39d in accordance with control of the ring movement controller 40. Accordingly, the ring 12a moves forward and backward relative to the housing 11a in the z-direction.

The radiation tomography apparatus 9 according to Embodiment 1 further includes each section for acquiring sectional images of the subject M, as shown in FIG. 1. Specifically, the radiation tomography apparatus 9 includes a filter 20 for extracting effective data from detection data detected in the detector ring 12; a coincidence section 21 that receives the data determined as the effective data in the filter 20 and performs coincidence of an annihilation gamma-ray pair; an LOR specifying section 23 for specifying an incident position of gamma rays in the detector ring 12 based on two pieces of gamma-ray detection data determined to be an annihilation gamma-ray pair in the coincidence section 21; a data storage section 24 for storing the detection data; a mapping section 25 for generating a sectional image of the subject M; and a calibration section 26 for performing calibration to the sectional image of the subject M. The calibration section 26 removes a false image falling in the sectional image with reference to a map stored in a calibration data storage section 34. The coincidence section corresponds to the coincidence device in this invention.

The filter 20 is provided for disposing of unnecessary detection data. Radiation that two scintillation counter crystals capture is considered a single radiation pair. However, where coincidence is performed to every combination of scintillation counter crystals, data processing becomes extremely complicated. Then, the filter 20 selectively pass to the coincidence section 21 a radiation pair in which two scintillation counter crystals capturing the radiation pair are not largely spaced away in the z-direction.

The radiation tomography apparatus 9 according to Embodiment 1 further includes a main controller 35 for controlling each section en bloc, and a display unit 36 for displaying a radiological image. The main controller 35 is formed of a CPU, and performs execution of various programs to realize the filter 20, the coincidence section 21, the LOR specifying section 23, the data storage section 24, the mapping section 25, and the calibration section 26. The above sections may each be divided into a controller that performs their functions.

<Operation of Radiation Tomography Apparatus>

Figure 6:
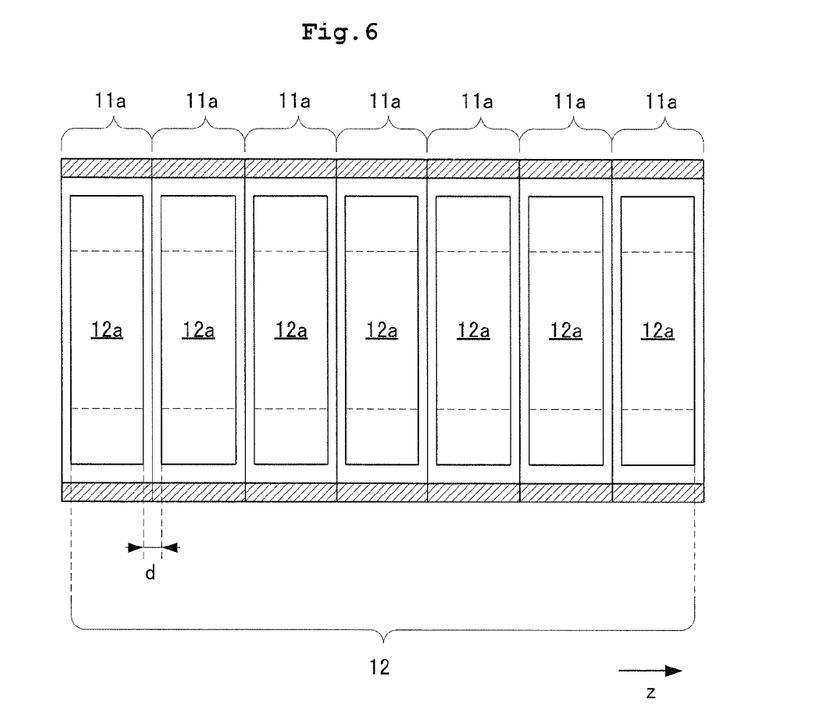
FIGS. 6 to 8 are sectional views each showing operation of the radiation tomography apparatus according to Embodiment 1.

Next, description will be given of operations of radiation tomography apparatus 9 as the most characteristic feature in Embodiment 1. FIG. 6 is a sectional view showing operation of the radiation tomography apparatus according to Embodiment 1. In an initial state of the radiation tomography apparatus 9, adjacent rings 11a are spaced away by a given clearance d (e.g., 5 cm), respectively. The center of the ring 12a in the z-direction conforms to the center of the housing 11a in the z-direction. That is, the ring 12a has a width in the z-direction that is smaller than the housing 11a. Here, FIG. 6 shows a state where each ring 12a is housed in the housing 11a without protruding in the z-direction, which state is referred to as a "housing state".

Figure 7:
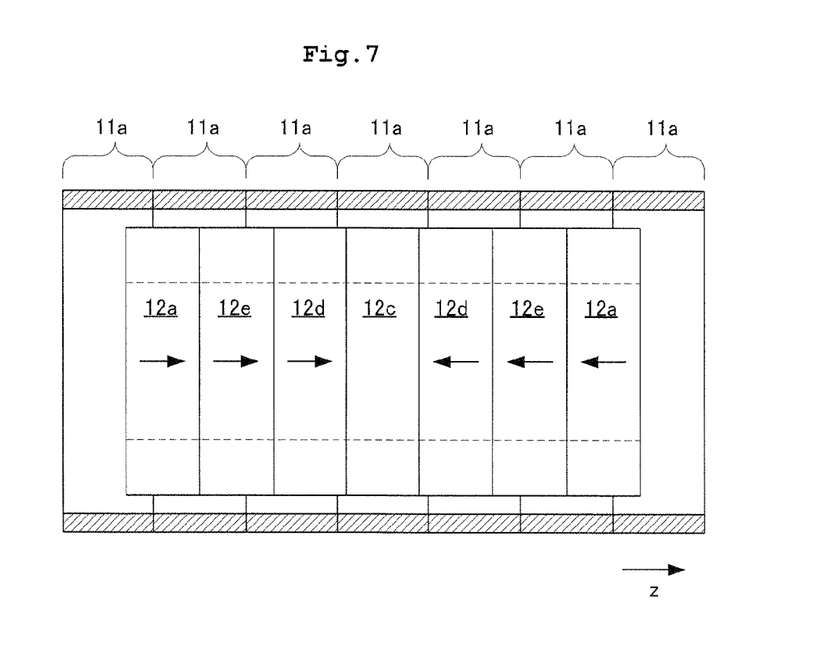

The operator provides instructions via the input unit 38 to connect the rings 12a from this state. Then, as shown in FIG. 7, the ring movement control section 40 controls the ring moving mechanism 39 to move six rings 12a, other than the center ring 12c at the center of the detecting ring 12, as to gather toward the center ring 12c. In so doing, the clearance d between each of the ring 12a is closed and disappears, and the rings 12a are each connected. In. FIG. 7, the quasi-center ring 12d among the rings 12a is adjacent to the center ring 12c, and corresponds to the second ring in this invention. The periphery ring 12e among the rings 12a interposes the quasi-center ring 12d with the center ring 12c, and corresponds to the first ring in this invention.

Each of the rings 12a gathers toward the center ring 12c, whereby a moving distance of the rings 12a located at the ends of the detector ring 12 in the z-direction may possibly be reduced. In FIG. 6, there exist two rings 12a and three clearances between the ring 12a at the most backward end in the z-direction and the center ring 12a. Consequently, the ring 12a in FIG. 7 merely moves by a distance three times the given clearance d (i.e., approximately 15 cm.) In so doing, the ring moving mechanism 39 may be achieved having a simple configuration. Even if the other rings 12a gather toward the ring 12a at the most forward end in the z-direction, the ring 12a at the most backward end in the z-direction has to move by a distance six times the given clearance d.

Here, the ring 12 moves relatively to the gantry 11a. Consequently, each housing 11a does not vary in position according to movement of the ring 12a.

Moreover, when the operator provides instructions via the input unit 38 to space away the rings 12a, the state in FIG. 7 (the connection state) returns to the state in FIG. 6. Such instructions are provided, for example, for separating the connected rings 12a and replacing the ring 12a when the radiation detector I forming the ring 12a is out of order.

Figure 8:
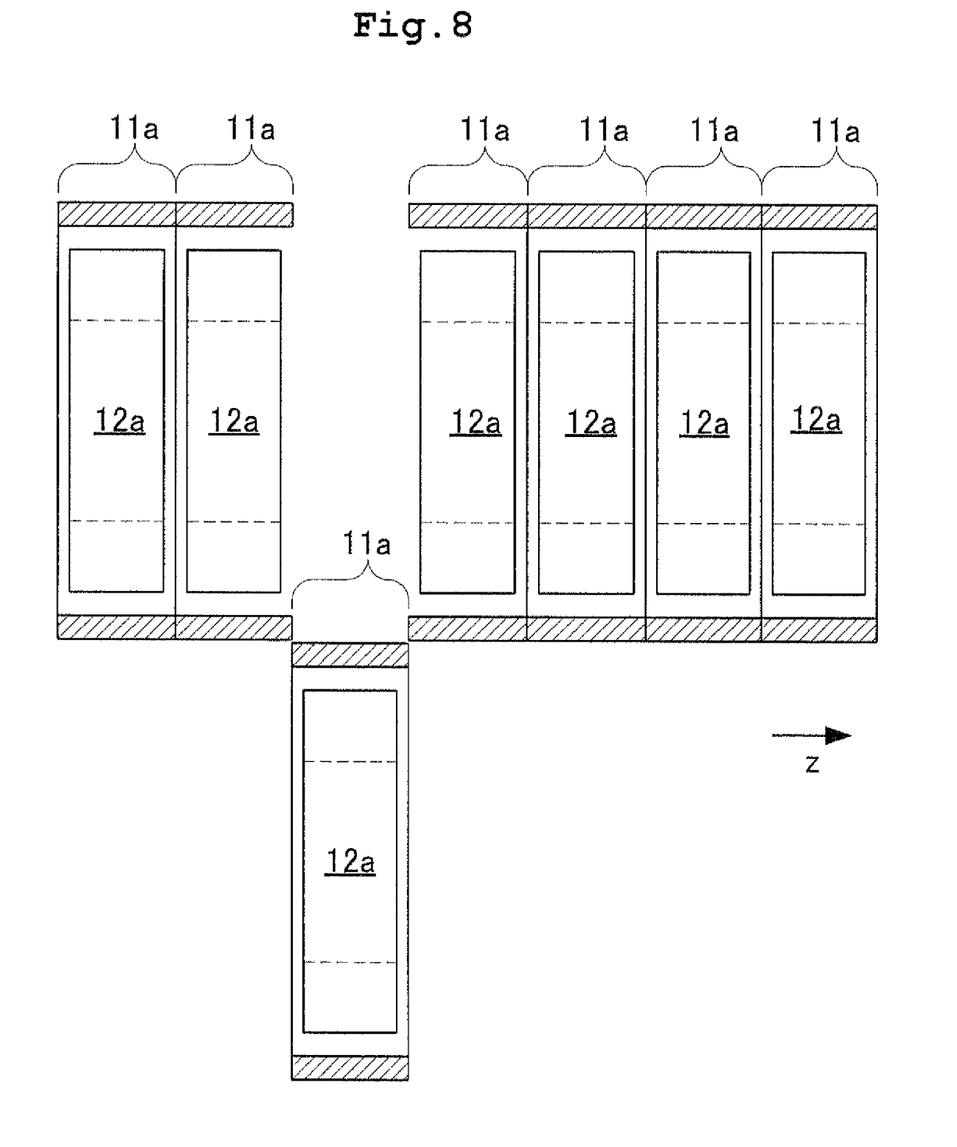

That is, each housing 11a is mechanically removable. As shown in FIG. 8, when the housing 11a is pulled out in a direction perpendicular to the z-direction, the ring 12a contained in the housing 11a is drawn out. Consequently, when breakdown of the radiation detector 1 occurs inside of the detector ring 12, the broken radiation detector 1 may be pulled out with the ring 12a. Accordingly, easier maintenance to the radiation tomography apparatus 9 may be realized.

<Inspection With Radiation Tomography Apparatus>

Now, description will be given of an inspection method using such radiation tomography apparatus. Upon conducting of examinations with the radiation tomography apparatus 9 according to Embodiment 1, firstly the subject M with radiopharmaceutical administered thereto by injection in advance is laid on the top board 10. Then, the top board 10 slides to move the subject M into an opening of the gantry 11. From here, the annihilation gamma-ray pair emitted from the subject M is detected. Here, a site to be imaged of the subject M is completely housed inside the gantry 11. The top board 10 does not move during radiation detection.

The coincidence section 21 performs coincidence successively to detection data outputted from the detector ring 12 to conduct pairing to an annihilation radiation pair. The LOR specifying section 23 specifies a position in the detector ring 12 where the annihilation radiation pair enters. Specifically, where two radiation photons are detected at two different positions in the detector ring 12 within a given time window, the two radiation photons are considered to enter into the detector ring 12 coincidently, and to be a single annihilation radiation pair. The time radiation enters into the detector ring 12 is determined in accordance with time information that the clock 19 adds to a detection signal. The data outputted from the coincidence section 21 and the LOR specifying section 23 is stored in the data storage section 24. The data storage section 24 stores a number of times that the coincidence section outputs detection data for each LOR (Line of response: a line connecting two scintillation counter crystals that detect a radiation pair) specified with the coincidence section. The data storage section 24 stores a number of times that an annihilation gamma ray pair is measured per LOR (a number of coincidence events.) The data storage section 24 stores the LOR and the number of counting annihilation gamma ray pairs that are associated with each other. The mapping section 25 constructs the associated data to acquire a sectional image (PET image.) The sectional image of the subject M generated as above is outputted to the calibration section 26. The calibration section 26 performs data processing for removing the false image superimposed on the sectional image of the subject M. The display unit 36 displays a completion image acquired in this way. As noted above, an inspection with the radiation tomography apparatus 9 according to Embodiment 1 is to be completed.

As noted above, the detector ring 12 in the radiation tomography apparatus 9 in Embodiment 1 includes the periphery rings 12e and the quasi-center rings 12d. The periphery rings 12e and the quasi-center rings 12d are each contained in the housing 11a. The housings Ha are connected to form the gantry 11. With such configuration, merely arranging housings 11a may realize expansion of the field of view. According to Embodiment 1, two or more conventional detector rings are connected to manufacture radiation tomography apparatus 9 having a large field of view.

Moreover, the periphery ring 12e moves as to approach the quasi-center ring 12d, whereby both the rings are connected. Such configuration may provide radiation tomography apparatus 9 with high sensitivity. If radiation tomography is conducted while a clearance is provided between both the rings, some radiation emits from the detector ring 12 through the clearance. Such radiation does not enter into the radiation detector 1, and thus is not observed. Accordingly, the detector ring 12 has poor detection sensitivity due to the clearance. On the other hand, according to Embodiment 1, the periphery ring 12e moves as to approach the quasi-center ring 12d, which results in a narrower clearance. Accordingly, radiation that is not observed may be reduced as much as possible.

Moreover, the housings 11a in Embodiment 1 are connected in the z-direction. A positional relationship between the housings Ha containing the periphery rings 12e does not vary independently of movement of the periphery rings 12e. Specifically, the periphery ring 12e moves relative to the gantry 11a, whereby the rings 12a to 12e are connected. The gantry 11a does not vary in position to connect the rings 12a to 12e. In other words, in the radiation tomography apparatus 9 according to Embodiment 1, the periphery ring 12e moves toward the quasi-center ring 12d in the gantry 11. Accordingly, the ring moving mechanism 39 for moving the periphery ring 12e may be reduced in size.

Moreover, each housing 11a in Embodiment 1 is mechanically removable.

For instance, when there arises a need to replace the periphery ring 12e, the housings Ha are disconnected from each other. Consequently, the periphery ring 12e contained in the housing 11a may be drawn out. That is, the housing 11a is pulled out relative to the next housing 11a in a direction perpendicular to the z-direction, whereby the periphery ring 12e is drawn out. The periphery ring 12e is spaced away from the quasi-center ring 12d, and a given clearance d is provided between the rings 12a to 12e. Then, the housing 11a is pulled out as shown in FIG. 8 in the direction perpendicular to the z-direction. Consequently, no interference of the periphery ring 12e occurs with the next housing 11a. Such configuration may provide radiation tomography apparatus 9 with easier maintenance.

Specifically, the periphery ring 12e, the quasi-center ring 12d, and the center ring 12c are spaced away by the given clearance d. The periphery ring 12e and the quasi-center ring 12d synchronously move as to approach the center ring 12c, whereby the three rings are connected. In other words, the ring movement control section 40 controls each ring en bloc, which leads to simpler control thereof. Such configuration as in Embodiment 1 may provide radiation tomography apparatus 9 with easier control.

Here, it is assumed that there arises a need to replace the radiation detector 1 forming the quasi-center ring 12d that is out of order. The connected three rings are spaced away, and the quasi-center ring 12d is contained in the housing 11a. When the housing 11a is pulled out under this state, the quasi-center ring 12d may be easily drawn out.

Moreover, the ring 12a in Embodiment 1 has a width in the z-direction that is smaller than the housing 11a in the z-direction. Consequently, no interference of the ring 12a occurs with the next housing 11a upon pulling out of the housing 11a for the purpose of maintenance.

EMBODIMENT 2

Next, description will be given of a PET/CT device according to Embodiment 2. The PET/CT device includes the radiation tomography apparatus (PET device) 9 described in Embodiment 1 and Embodiment 2, and a CT device for generating a sectional image using X-rays, and is medical apparatus that allows generation of a composite image having superimposed sectional images acquired in both devices.

Figure 9:
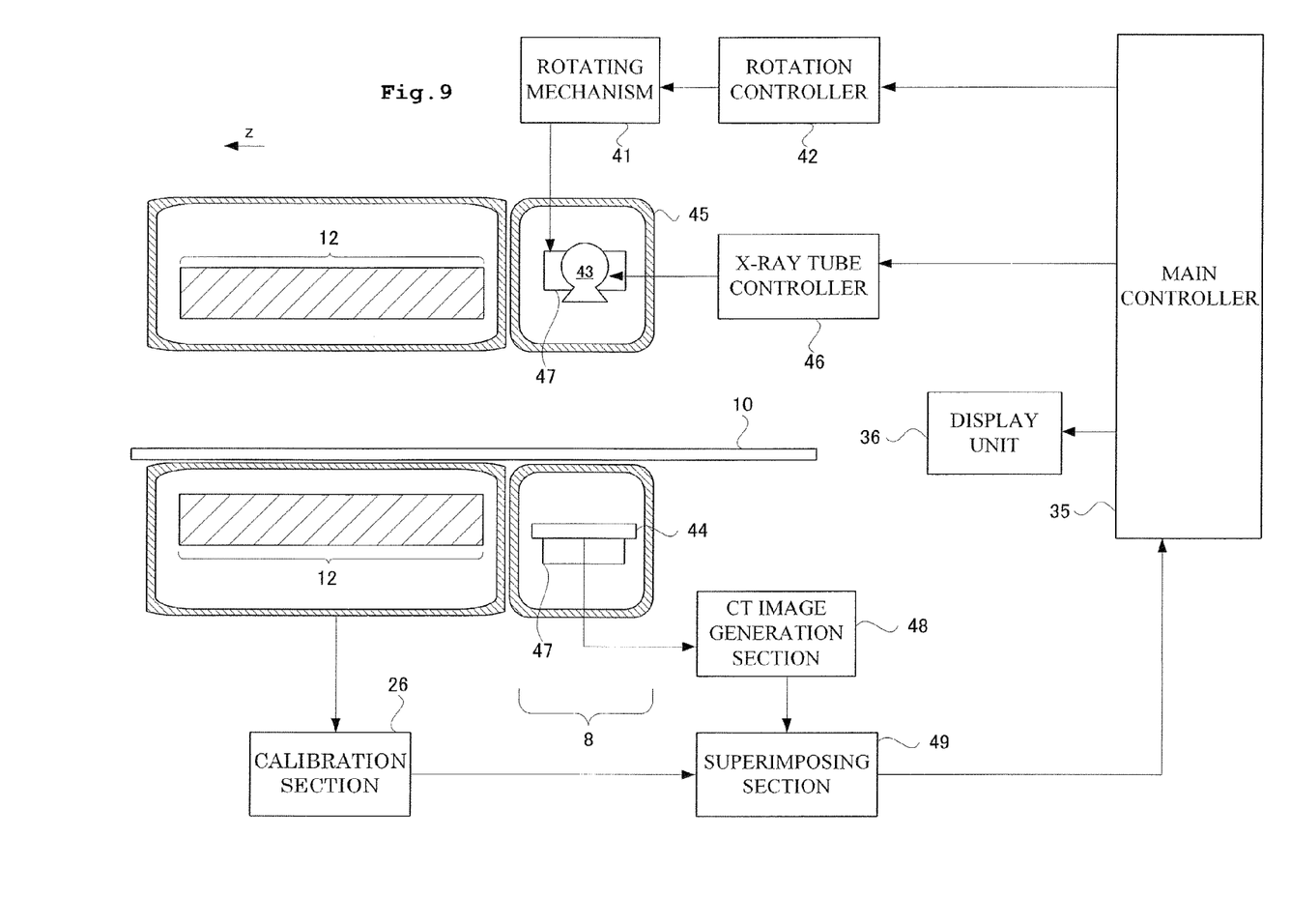
FIG. 9 is a functional block diagram showing a configuration of radiation tomography apparatus according to Embodiment 2.

Here, description will be given of a configuration of the PET/CT device according to Embodiment 2. The radiation tomography apparatus (PET device) 9 described in Embodiment 1 or Embodiment 2 may be used for the PET/CT device according to Embodiment 2. Consequently, description will be given of the CT device as a characteristic portion in Embodiment 2. As shown in FIG. 9, the CT device 8 has a gantry 45. The gantry 45 is provided with an opening that extends in the z-direction with a top board 10 inserted therein.

The gantry 45 has inside thereof an X-ray tube 43 for irradiating a subject M with X-rays, an FPD (flat panel detector) 44, and a support portion 47 for supporting the X-ray tube 43 and the FPD 44. The support portion 47 has a ring shape, and freely rotates about the z-axis. A rotating mechanism 41 formed of a power generation device such as a motor and a power transmission device such as a gear performs rotation of the support portion 47. A rotation controller 42 controls the rotating mechanism 41. The X-ray tube corresponds to the radiation source in this invention. The FPD corresponds to the radiation detecting device in this invention. The support portion corresponds to the support device in this invention. The rotating mechanism corresponds to the rotating device in this invention. The rotation controller corresponds to the rotation control device in this invention.

The CT image generation section 48 generates an X-ray sectional image of the subject M in accordance with X-ray detection data outputted from the FPD 44. The superimposing section 49 generates a superimposed image through superimposing the above X-ray sectional image and a PET image showing radiopharmaceutical distribution in the subject M that is outputted from the radiation tomography apparatus (PET device) 9.

The main controller 35 performs execution of various programs to realize the mapping section 25, the calibration section 26 according to Embodiment 1 and Embodiment 2 as well as the rotation controller 42, the CT image generation section 48, the superimposing section 49, and the X-ray tube controller 46. The above sections may each be divided into a controller that performs their functions.

Now, description will be given of a method for acquiring an X-ray fluoroscopic image. The X-ray tube 43 and the FPD 44 rotates about the z-axis while a relative position therebetween is maintained. Here, the X-ray tube 43 intermittently irradiates the subject M with X-rays, and the CT image generation section 48 generates an X-ray fluoroscopic image for every irradiation. The two or more X-ray fluoroscopic images are constructed into a single sectional image with use of an existing back projection method, for example, in the CT image generation section 48.

Next, description will be given of a method of generating the composite image. In order to acquire the composite image with the PET/CT device, the site of interest in the subject M is introduced into the CT device to acquire an X-ray sectional image thereof. In addition to this, the site of interest in the subject M is introduced into the radiation tomography apparatus (PET device) 9 to acquire a PET image. The superimposing section 49 superimposes both images for completing the composite image. The display unit 36 displays the composite image. Accordingly, radiopharmaceutical distributions and the internal subject structure may be recognized simultaneously, which may result in provision of the sectional image suitable for diagnosis.

According to Embodiment 2 as above, the radiation tomography apparatus 9 may be provided that allows acquisition of both images of pharmaceutical distribution and the internal subject structure. In general, a PET device may obtain information on pharmaceutical distribution. However, it may sometimes be necessary to conduct diagnosis referring to the sectional image having internal organs and tissue of the subject falling therein. According to the above configuration, both images of the internal structure of the subject M and pharmaceutical distribution may be acquired. Consequently, superimposing both images may realize generation of a composite image suitable for diagnosis.

This invention is not limited to the foregoing configuration, but may be modified as follows.

(1) In each embodiment, coincidence is performed when the rings 12a are in the connection state as shown in FIG. 6. Alternatively, coincidence may be performed when the rings 12a to 12e are in the housing state as shown in FIG. 7. With the above configuration, various types of methods for detecting radiation may be achieved. That is, the radiation tomography apparatus 9 may count the number of radiation pairs under any of the housing state and the connection state. In other words, radiation may be detected under any of both the states. Simply in the light of increasing a dose of radiation to be detected, it is preferable for the periphery ring 12e to be in the connection state when images are taken. On the other hand, a clearer sectional image having reduced noises may sometimes be acquired when the periphery ring 12e is under the housing state depending on distribution of occurrence sites of radiation in the subject M. In one modification as above, the characteristic that the periphery ring 12e moves may efficiently be employed also in taking a radiation tomography image.

(2) In addition to both the states, coincidence may be performed under an intermediate state of both the states (an intermediate state between those in FIG. 6 and FIG. 7.) Accordingly, more various types of methods for detecting radiation may be achieved. A clearer sectional image having reduced noises may sometimes be acquired under the intermediate state. According to this modification, the state of the rings 12a to 12e suitable for imaging may be searched for.

Moreover, in Embodiment 1, radiation may be detected while the housing state, the connection state, and the intermediate state are repeated.

(3) Moreover, in addition to the configuration in each embodiment, a ring position acquiring section 17 for acquiring a position of the ring in FIG. 1, and a positional information correction section 22 for correcting positional information on a radiation pair outputted from each of the rings 12a to 12e in accordance with positional information from the ring position acquiring section 17 may be adopted. That is, the rings 12a to 12e each move relative to the subject M. Accordingly, a position indicated by information on the radiation pair that is outputted from the rings 12a to 12e is shifted relative to the subject M. In Embodiment 1, the positional information outputted from the rings 12a to 12e is corrected in accordance with the position of the rings 12a to 12e, whereby a position of the radiation pair relative to the subject M may be acquired. In so doing, a radiation tomography image having no distortion may be acquired without influences of movement of the rings 12a to 12e when radiation is detected while the rings 12a to 12e move relative to the subject M. The ring position acquiring section 17 acquires positional information on the rings 12a to 12e through acquisition of data on control of the ring movement from the ring movement controller 40 in FIG. 4. The positional information correcting section corresponds to the positional information correction device in this invention. The ring position acquiring section corresponds to the ring position acquiring device in this invention.

(4) In each of the foregoing embodiments, the scintillation counter crystal is composed of LYSO. Alternatively, the scintillation counter crystal may be composed of another materials, such as GSO ($Gd_2SiO_5$), may be used in this invention. According to this modification, a method of manufacturing a radiation detector may be provide that allows provision of a radiation detector of low price.

(5) The fluorescence detector in each of the foregoing embodiments is formed of the photomultiplier tube. This invention is not limited to this embodiment. A photodiode, an avalanche photodiode, a semiconductor detector, etc., may be used instead of the photomultiplier tube.

(6) In the foregoing embodiment, the top board is freely slidable. This invention is not limited to this. For instance, the top board may be fixed, whereas the gantry 11 may slide.

[Industrial Utility]

As described above, this invention is suitable for radiation tomography apparatus for medical uses.

The invention claimed is:

1. Radiation tomography apparatus comprising:
   a first ring having radiation detectors for detecting radiation from a subject annularly arranged:
   a second ring having the radiation detectors annularly arranged;
   a gantry for containing both the rings;
   a first moving device for moving the first ring relative to the gantry; and
   a movement control device for controlling the first moving device,
   both the rings being spaced away by a given clearance as to share each central axis,
   the first ring moving as to approach the second ring in connection with control by the movement control device, whereby both the rings are connected, and
   the gantry comprises a first housing for containing the first ring, and a second housing for containing the second ring, both the housings being mechanically removable.

2. The radiation tomography apparatus according to claim 1, wherein the gantry is held stationary when the first ring moves.

3. The radiation tomography apparatus according to claim 2, comprising:
   a third ring having the radiation detectors annularly arranged; and
   a second moving device for moving the second ring relative to the second housing,
   the first ring, the second ring, and the third ring being spaced away in this order by a given clearance as to share each central axis, and
   the first ring and the second ring synchronously moving as to approach the third ring through control by the movement control device, whereby the three rings are connected.

4. The radiation tomography apparatus according to claim 2, wherein
   the first ring has a width in the central axis that is smaller than the first housing in the central axis.

5. The radiation tomography apparatus according to claim 2, comprising:
   a coincidence device for performing coincidence of radiation pairs, wherein
   the first moving device moves the first ring such that a housing state and a connection state are alternately repeated, the housing state being a state where the first ring is housed in the first housing and the connection state being a state where the first ring is connected to the second ring, and
   the coincidence device counts a number of radiation pairs when the first ring is in either of both the states.

6. The radiation tomography apparatus according to claim 5, wherein
   the coincidence device counts the number of radiation pairs under an intermediate state between both the states in addition to both the states.

7. The radiation tomography apparatus according to claim 6, comprising:
   a ring position acquiring device for acquiring a position of the first ring; and
   a positional information correction device for correcting positional information on a radiation pair outputted from the first ring in accordance with positional information from the ring position acquiring device.

8. The radiation tomography apparatus according to claim 1, comprising:
   a third ring having the radiation detectors annularly arranged; and
   a second moving device for moving the second ring relative to the second housing,
   the first ring, the second ring, and the third ring being spaced away in this order by a given clearance as to share each central axis, and
   the first ring and the second ring synchronously moving as to approach the third ring through control by the movement control device, whereby the three rings are connected.

9. The radiation tomography apparatus according to claim 8, wherein
   the first ring has a width in the central axis that is smaller than the first housing in the central axis.

10. The radiation tomography apparatus according to claim 8, comprising:
    a coincidence device for performing coincidence of radiation pairs, wherein
    the first moving device moves the first ring such that a housing state and a connection state are alternately repeated, the housing state being a state where the first ring is housed in the first housing and the connection state being a state where the first ring is connected to the second ring, and
    the coincidence device counts a number of radiation pairs when the first ring is in either of both the states.

11. The radiation tomography apparatus according to claim 10, wherein
    the coincidence device counts the number of radiation pairs under an intermediate state between both the states in addition to both the states.

12. The radiation tomography apparatus according to claim 11, comprising:
    a ring position acquiring device for acquiring a position of the first ring; and
    a positional information correction device for correcting positional information on a radiation pair outputted from the first ring in accordance with positional information from the ring position acquiring device.

13. The radiation tomography apparatus according to claim 1, wherein
    the first ring has a width in the central axis that is smaller than the first housing in the central axis.

14. The radiation tomography apparatus according to claim 13, comprising:
    a coincidence device for performing coincidence of radiation pairs, wherein
    the first moving device moves the first ring such that a housing state and a connection state are alternately repeated, the housing state being a state where the first ring is housed in the first housing and the connection state being a state where the first ring is connected to the second ring, and
    the coincidence device counts a number of radiation pairs when the first ring is in either of both the states.

15. The radiation tomography apparatus according to claim 14, wherein
    the coincidence device counts the number of radiation pairs under an intermediate state between both the states in addition to both the states.

16. The radiation tomography apparatus according to claim 15, comprising:
    a ring position acquiring device for acquiring a position of the first ring; and
    a positional information correction device for correcting positional information on a radiation pair outputted from the first ring in accordance with positional information from the ring position acquiring device.

17. The radiation tomography apparatus according to claim 1, comprising:
    a coincidence device for performing coincidence of radiation pairs, wherein
    the first moving device moves the first ring such that a housing state and a connection state are alternately repeated, the housing state being a state where the first ring is housed in the first housing and the connection state being a state where the first ring is connected to the second ring, and
    the coincidence device counts a number of radiation pairs when the first ring is in either of both the states.

18. The radiation tomography apparatus according to claim 17, wherein the coincidence device counts the number of radiation pairs under an intermediate state between both the state in addition to both the states.

19. The radiation tomography apparatus according to claim 18, comprising:
  a ring position acquiring device for acquiring a position of the first ring; and
  a positional information correction device for correcting positional information on a radiation pair outputted from the first ring in accordance with positional information from the ring position acquiring device.

20. The radiation tomography apparatus according to claim 1, further comprising:
  a top board that extends in the central axis direction and is inserted into an inside portion of the detector ring, the radiation tomography apparatus further comprising an image generation device including:
    (A) a radiation source that allows rotation relative to the top board around the central axis;
    (B) a radiation detecting device that allows rotation relative to the top board around the central axis;
    (C) a support device for supporting the radiation source and the radiation detecting device;
    (D) a rotating device for rotating the support device; and
    (E) a rotation control device for controlling the rotating device.

* * * * *